United States Patent [19]
Laurent et al.

[11] Patent Number: 6,011,060
[45] Date of Patent: Jan. 4, 2000

[54] CHIRAL PHENYLDIHYDROFURANONES AS PDE-IV INHIBITORS

[75] Inventors: Henry Laurent; Peter Esperling; Kurt Hamp; Herbert Schneider; Helmut Wachtel, all of Berlin, Germany

[73] Assignee: Schering Aktiengesellschaft, Berlin, Germany

[21] Appl. No.: 09/171,632

[22] PCT Filed: Apr. 22, 1997

[86] PCT No.: PCT/DE97/00826

§ 371 Date: Dec. 11, 1998

§ 102(e) Date: Dec. 11, 1998

[87] PCT Pub. No.: WO97/40032

PCT Pub. Date: Oct. 30, 1997

[30] Foreign Application Priority Data

Apr. 23, 1996 [DE] Germany .............. 196 17 864

[51] Int. Cl.$^7$ .................................. A61K 31/34
[52] U.S. Cl. ............................ 514/473; 549/323
[58] Field of Search ............... 549/323; 514/473

[56] References Cited

FOREIGN PATENT DOCUMENTS

| | | |
|---|---|---|
| 2655369 | 6/1978 | Germany . |
| 2745320 | 4/1979 | Germany . |
| WO87/06576 | 11/1987 | WIPO . |
| WO 92/07567 | 5/1992 | WIPO . |
| WO 94/06423 | 3/1994 | WIPO . |
| WO 97/40032 | 10/1997 | WIPO . |

OTHER PUBLICATIONS

Lienne, M. et al Optimization of Direct Chiral Separation of Potential Cytoloxic Alpha–Methylene–Gamma Butyrolactones and Alpha–Methylene–Gamma Butyrolactams by Liquid Chromatography. CA 110:127899, 1989.

*Primary Examiner*—Amelia Owens
*Attorney, Agent, or Firm*—Millen, White, Zelano & Branigan

[57] ABSTRACT

Described are racemic and enantiomerically pure chiral phenyldihydrofuranones, their preparation and their use in drugs (selective inhibition of the cAMP-specific phosphodiesterase IV).

19 Claims, No Drawings

CHIRAL PHENYLDIHYDROFURANONES AS PDE-IV INHIBITORS

The invention relates to new chiral phenyldihydrofuranone derivatives, the process for their production and their use as pharmaceutical agents.

It is known that selective inhibitors of the cAMP-specific phosphodiesterase IV (CAMP-PDE IV inhibitors) have pharmacological properties, on the basis of which they represent suitable active ingredients in pharmaceutical agent preparations. To improve the action, numerous modifications were carried out on the molecule without, however, achieving the desired increase of action.

It has now been found, surprisingly enough, that the compounds of formula I represent very potent selective cAMP-PDE IV inhibitors, which are metabolically very stable.

The invention relates to racemic and enantiomer-pure compounds of formula I,

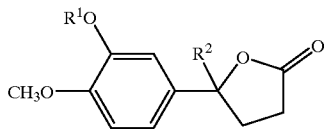
(I)

in which
R$^1$ means a hydrocarbon radical with up to 8 C atoms and R$^2$ means C$_{1-4}$ alkyl.

As hydrocarbon radical R$^1$, alkyl, alkenyl, alkinyl, cycloalkyl and cycloalkylalkyl are suitable.

Alkyl radical R$^1$ preferably has up to 6 carbon atoms and can be straight-chain or branched like alkyl radical R$^2$, such as, for example, methyl, ethyl, propyl, isopropyl, butyl, sec-butyl, isobutyl, tert-butyl, pentyl, 2-methyl-butyl, 2,2-dimethylpropyl and hexyl.

If the hydrocarbon radical means alkenyl or alkinyl, for example vinyl, 1-propenyl, 2-propenyl, 3-methyl-2-propenyl and 2-propinyl with up to 4 C atoms can thus be mentioned.

The cycloalkyl radical has 3–7 C atoms, such as, for example, cyclopropyl, cyclobutyl, cyclopentyl, cyclohexyl or cycloheptyl.

As cycloalkylalkyl radical R$^2$, C$_{3-7}$ cycloalkyl-C$_{1-2}$ alkyl is suitable, in the same way as, for example, cyclopropyl methyl, cyclopropyl ethyl, cyclopentyl methyl, i.a., are suitable.

The compounds of formula I contain one or more chiral centers and comprise the racemic diastereomeric mixtures as well as the individual isomers.

The subject matter of the invention is also the process for the production of compounds of formula I and their isomers.

The production of the compounds of formula I is characterized in that a compound of formula II

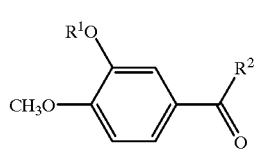
(II)

in which R$^1$ and R$^2$ have the above meaning, is reacted with an acrylic acid ester in the presence of samarium(II) iodide and a proton donor, and optionally then the isomers are separated.

The coupling of the acrylic acid ester and a compound of formula II that is induced by samarium(II) iodide is generally carried out at room temperature, by 2 molar equivalents of samarium(II) iodide and 1 molar equivalent of substrate being reacted in a solvent. As a solvent, especially tetrahydrofuran is suitable. Samarium(II) iodide in a 0.1 molar solution in THF, stabilized with samarium powder, can be ordered from the Aldrich Company. The addition of an alcohol as a proton donor, such as, for example, methanol, ethanol or tert-butanol, prevents the development of by-products and makes possible the production of the compounds according to the invention under mild conditions in very good yield. The reaction can be completed after a few minutes or else several hours.

By adding an additive such as tetramethylethylenediamine or hexamethylphosphorus amide, the reaction rate can be elevated, and the yield can be increased. As esters of acrylic acid, especially alkyl esters are suitable, but other esters can also be used.

The isomers can be separated into enantiomers according to commonly used methods, such as, for example, chromatography, crystallization or conversion into diastereomer mixtures with chiral adjuvants. The optically active phenyldihydrofuranones of formula I can be obtained from the corresponding racemates by chromatography on chiral columns.

The new compounds of formula I and their isomers are inhibitors of phosphodiesterase IV and, via the specific intervention in the cAMP metabolism, affect the signal function of this important intracellular transmitter, which represents the molecular substrate for information transfer in a large number of biochemical reactions. The various subaspects of the profile of action can be attributed to this pharmacological base mechanism, which provides a basis for explanation, i.a, for the antiinflammatory effect and the good neuropsychotropic action.

On the basis of their profile of action, the compounds of formula I are suitable for the treatment of neurodegenerative diseases such as dementia, Parkinson's disease, depression, inflammatory diseases such as arthritis, shock, sepsis, pulmonary diseases, bone resorption diseases, HIV infection, cerebral malaria, multiple sclerosis, and inflammatory skin diseases. The compounds according to the invention also show broncho-spasmolytic, antiproliferative, platelet-aggregation-inhibiting and tocolytic properties.

The compounds of formula I also inhibit TNF production and are therefore suitable for the treatment of diseases that are mediated via the activation of TNF.

Diseases that are mediated by TNF are defined both as diseases that are triggered by production of TNF and diseases in which other cytokines, such as, for example, Il-1 or Il-6, are affected by TNF.

TNF is defined both as TNF-α and TNF-β, which both are antagonized by the compounds of formula I. TNF-α is preferably inhibited.

The compounds of formula I are therefore suitable for the production of a pharmaceutical preparation, which is used for the treatment and prophylaxis of diseases in living creatures, which are triggered by stimulation of TNF. As diseases that are affected by excessive or unregulated TNF stimulation, for example, allergic and inflammatory diseases, auto-immune diseases, pulmonary diseases, infectious diseases and bone resorption diseases are known, such as rheumatoid arthritis, rheumatoid spondylitis, osteoarthritis, gout, sepsis, septic shock, endotoxin shock, gram-negative sepsis, toxic shock syndrome, ARDS (acute respiratory distress syndrome), pulmonary sarcoidosis, asthma, chronic bronchitis, allergic rhinitis, conjunctivitis, fibrosis, including cystic fibrosis, and arteriosclerosis, pyresis, pains, glomerulonephritis, silicosis, cachexia, colitis ulcerosa, colitis granulomatosa, Crohn's disease, osteoporosis, organ damage after reperfusion.

The compounds are also suitable for the treatment of infectious diseases such as viral infections with, for example, HIV, Borna, Epstein-Barr, measles, arbovirus pathogens, especially of the central nervous system; parasitic infections, such as, e.g., cerebral malaria, fever, myalgia, HIV, AIDS, cachexia and bovine insanity. Other diseases, which can be treated with the compounds of formula I, are multiple sclerosis, leprosy, diabetes mellitus, diabetes insipidus, leukemia, panencephalitis, cerebral disorders such as depression, senile dementia, multiinfarct, dementia and stroke. The compounds of formula I can also be used for the treatment of inflammatory skin diseases, such as, for example, psoriasis, urticaria, atopic dermatitis, allergic rhinitis, contact dermatitis, rheumatic arthritis, lupus erythematosus, sunburn, and eczema.

The action of the compounds of formula I in the above-mentioned indications can be shown by corresponding, commonly used pharmacological tests as indicated by the head twitching and grooming reaction in rats that is characteristic of phosphodiesterase type IV (PDE IV) inhibitors. The compound is administered intraperitoneally (i.p.) to male Wistar rats, and the occurrence of head twitching and grooming is detected by observation for 15–75 minutes after injection.

The action on the central nervous system is determined in vitro by measuring the displacement capacity of radiolabeled Rolipram of rat brain homogenates (Eur. J. Pharmacol., Vol. 127, 105–115 (1986)). The $IC_{50}$ values (that concentration in which 50% inhibiting action occurs) were converted into inhibition constant $K_i$, which is calculated according to the formula below:

$$K_i = IC_{50}/[1+(L/K_D)],$$

in which L means the concentration of the radioactive tracer and $K_D$ means the dissociation constant of the $^3$H-rolipram bond, which is determined separately.

TABLE (R)-(+)-isomer (S)-(-)-isomer

| R | Racemate $K_i$ [nM] | (R)-(+)-enantiomer $K_i$ [nM] | (S)-(-)-enantiomer $K_i$ [nM] |
|---|---|---|---|
| propyl | 0.74 | 7.30 | 0.47 |
| cyclopropyl methyl | 0.21 | 2.20 | 0.13 |
| isobutyl | 0.48 | 2.30 | 0.25 |
| cyclobutyl | 0.38 | 1.90 | 0.20 |
| cyclopentyl | 0.50 | 2.80 | 0.28 |

The agents are produced according to commonly used processes, by the active ingredient being brought with suitable vehicles, adjuvants and/or additives into the form of a pharmaceutical preparation, which is suitable for enteral or parenteral administration. The preparations thus obtained can be used as pharmaceutical agents in human or veterinary medicine. The administration can be carried out orally or sublingually as a solid in the form of capsules or tablets or as a liquid in the form of solutions, suspensions, elixirs, aerosols or emulsions or rectally in the form of suppositories, or in the form of injection solutions that can optionally also be administered subcutaneously, intramuscularly or intravenously, or topically or intrathecally. As adjuvants for the desired pharmaceutical agent formulation, the inert organic and inorganic media that are known to one skilled in the art, such as, e.g., water, gelatin, gum arabic, lactose, starch, magnesium stearate, talc, plant oils, polyalkylene glycols, etc., are suitable. Moreover, preservatives, stabilizers, wetting agents, emulsifiers or salts for altering osmotic pressure or buffers optionally can be contained.

The pharmaceutical preparations can be present in solid form, e.g., as tablets, coated tablets, suppositories, capsules or in liquid form, e.g., as solutions, suspensions or emulsions.

As vehicle systems, near-interface adjuvants such as salts, bile acids or animal or plant phospholipids and their mixtures as well as liposomes or their components can also be used.

For oral administration, especially tablets, coated tablets or capsules with talc and/or hydrocarbon vehicles or binders, such as, e.g., lactose, corn or potato starch, are suitable. The administration can also be carried out in liquid form, such as, e.g., as juice, to which optionally sweetener is added.

The compounds of formula I are used at dosages that are sufficient to reduce the TNF production to normal or small levels.

The dosage of the active ingredients can vary depending on method of administration, age and weight of the patient, type and severity of the disease to be treated and similar factors. The daily dose is 0.1–25 mg, preferably 0.5–5 mg, whereby the dose can be given as an individual dose to be administered once or divided into two or more daily doses.

In so far as the production of the starting compounds is not described, the latter are known from the literature or can be produced analogously to the known compounds or processes that are described here.

The following examples are to explain the process according to the invention.

Starting Compounds

3-Cyclopentyloxy-4-methoxyacetophenone

A solution of 2.0 g of 3-hydroxy-4-methoxyacetophenone in 60 ml of ethanol is mixed drop by drop with 2.0 ml of bromocyclopentane after 3.0 g of potassium carbonate is added while being stirred, and then it is heated to boiling under reflux for 5 hours. After the salts are filtered off, the solvent is evaporated in a vacuum, and the residue is distilled twice on a bulb tube at 170° C. and 0.15 mbar. Yield 2.4 g, melting point 56° C.

3-Cyclobutyloxy-4-methoxyacetophenone

A solution of 3.0 g of 3-hydroxy-4-methoxyacetophenone in 60 ml of anhydrous dimethylformamide is mixed under nitrogen with 1.31 g of a 55% sodium hydride oil suspension, and it is stirred for 30 minutes at 60° C. After 3.0 g of bromocyclobutane is added, the reaction mixture is heated for 3 hours to 110° C., then concentrated by evaporation to one-half its original volume in a vacuum and stirred into NaCl-containing ice water. It is extracted with diethyl ether, the extract is washed with water, dried on sodium sulfate and concentrated by evaporation in a vacuum. The oily residue is chromatographed on a silica gel column (Kromasil 100/10 μm) with a hexane-tert-butyl methyl ether mixture (4:1). 1.77 g is eluted, melting point 72° C.

3-Cyclopentylaxy-4-methoxy-propiophenons

A suspension of 1.1 g of magnesium in 5 ml of diethyl ether is mixed drop by drop with a solution of 3 ml of ethyl iodide in 11.5 ml of diethyl ether. The corresponding Grignard reagent is formed. A solution of 6.61 g of 3-cyclopentyloxy-4-methoxy-benzaldehyde in 65 ml of diethyl ether is added in drops to this solution within one hour. Then, the reaction mixture is mixed with 10 ml of saturated ammonium chloride solution, the precipitate that is produced in this case is suctioned off, and the filtrate, the ether phase, is dried on sodium sulfate and concentrated by evaporation in a vacuum. The residue, which consists of 6.5 g of crude 1-(3-cyclopentyloxy-4-methoxyphenyl)-propanol, is dissolved in 45 ml of pure acetone and mixed drop by drop with 7 ml of 8N Jones reagent while being cooled with ice. It is stirred for 15 minutes at room temperature, mixed with water and extracted with ethyl acetate. The extract is dried and concentrated by evaporation in a vacuum. The oily residue is chromatographed on a silica gel column (Kromasil 100/10 μm) with a hexane-tert-butyl methyl ether mixture (4:1). 5.23 g of 3-cyclopentyloxy-4-methoxy-propiophenone is eluted as an oily product.

EXAMPLE 1

5-(3-Cyclopentyloxy-4-methoxyphenyl)-5-methyl-dihydro-2-furanone

A. 100 ml of a 0.1 M solution of samarium(II) iodide in tetrahydrofuran is mixed, with oxygen carefully excluded, with the solution of 1.0 g of 3-cyclopentyloxy-4-methoxy-acetophenone, 500 mg of acrylic acid ethyl ester and 350 mg of tert-butanol in 10 ml of tetrahydrofuran. The reaction solution is mixed thoroughly, allowed to stand for 15 hours at room temperature and then poured into 100 ml of 20% hydrochloric acid. It is stirred for two hours at room temperature and extracted with diethyl ether. The ether phase is washed with sodium thiosulfate solution and water, dried on sodium sulfate and concentrated by evaporation in a vacuum. The residue, a yellow oil, is chromatographed on a silica gel column (Kromasil 100/10 μm) with a hexane-tert-butyl methyl ether mixture (4:1). 805 mg of crystalline (R,S)-5-(3-cyclopentyloxy-4-methoxyphenyl)-5-methyl-dihydro-2-furanone is eluted, melting point 59.6° C.

B. 500 mg of (R,S)-5-(3-cyclopentyloxy-4-methoxyphenyl)-5-methyl-dihydro-2-furanone is chromatographed on a ChiraSpher® phase (25 μm) with a hexane-dioxane mixture (15:1). 170 mg of (R)-(+)-5-(3-cyclopentyloxy-4-methoxyphenyl)-5-methyl-dihydro-2-furanone, oily, $[\alpha]_D=+24.5°$ (CHCl$_3$) as well as 220 mg of (S)-(−)-5-(3-cyclopentyloxy-4-methoxyphenyl)-5-methyl-dihydro-2-furanone, oily, $[\alpha]_D=-24.2°$ (CHCl$_3$), are eluted.

EXAMPLE 2

5-(4-Metboxy-3-propoxyphenyl)-5-methyl-dihydro-2-furanone

A. 100 ml of a 0.1 M solution of samarium(II) iodide in tetrahydrofuran is mixed, with oxygen carefully excluded, with the solution of 860 mg of 4-methoxy-3-propoxyacetophenone, 500 mg of methyl acrylate and 350 mg of tert-butanol in 5 ml of tetrahydrofuran. The reaction solution is mixed thoroughly, allowed to stand for two hours at room temperature and then poured into 100 ml of 20% hydrochloric acid. It is stirred for two hours at room temperature and extracted with diethyl ether. The ether phase is washed with sodium thiosulfate solution and water, dried on sodium sulfate and concentrated by evaporation in a vacuum. The oily residue is chromatographed on a silica gel column (Kromasil 100/10 μm) with a hexane-tert-butyl methyl ether mixture (4:1). 770 mg of (R,S)-5-(4-methoxy-3-propoxyphenyl)-5-methyl-dihydro-2-furanone is eluted, melting point 67.0° C.

B. 610 mg of (R,S)-5-(4-methoxy-3-propoxyphenyl)-5-methyl-dihydro-2-furanone is chromatographed on a ChiraSpher® phase (25 μm) with a hexane-dioxane mixture (15:1). 242 mg of (R)-(+)-5-(4-methoxy-3-propoxyphenyl)-5-methyl-dihydro-2-furanone, melting point 82.3° C., $[\alpha]_D=+27.4°$ (CHCl$_3$), as well as 190 mg of (S)-(−)-5-(4-methoxy-3-propoxyphenyl)-5-methyl-dihydro-2-furanone, melting point 83.3° C., $[\alpha]_D=-24.2°$ (CHCl$_3$), are eluted.

EXAMPLE 3

5-(3-Isobutyloxy-4-methoxyphenyl)-S-methyl-dihydro-2-furanone

A. 100 ml of a 0.1 M solution of samarium(II) iodide in tetrahydrofuran is mixed, with oxygen carefully excluded, with the solution of 1.35 g of 3-isobutyloxy-4-methoxyacetophenone, 850 mg of ethyl acrylate and 595 mg of tert-butanol in 10 ml of tetrahydrofuran. The reaction solution is mixed thoroughly, allowed to stand for 3 hours at room temperature and then poured into 100 ml of 20% hydrochloric acid. It is stirred for two hours at room temperature and extracted with diethyl ether. The ether phase is washed with sodium thiosulfate solution and water, dried on sodium sulfate and concentrated by evaporation in a vacuum. The oily residue is chromatographed on a silica gel column.(Kromasil 100/10 μm) with a hexane-tert-butyl methyl ether mixture (4:1). 890 mg of (R,S)-5-(3-isobutyloxy-4-methoxyphenyl)-5-methyl-dihydro-2-furanone is eluted as an oily product.

B. 500 mg of (R,S)-5-(3-isobutyloxy-4-methoxyphenyl)-5-methyl-dihydro-2-furanone is chromatographed on a ChiraSpher® phase (25 μm) with a hexane-dioxane mixture (15:1). 190 mg of (R)-(+)-5-(3-isobutyloxy-4-methoxyphenyl)-5-methyl-dihydro-2-furanone, oily, $[\alpha]_D$=+23.1° (CHCl$_3$), as well as 180 mg of (S)-(-)-5-(3-isobutyloxy-4-methoxyphenyl)-5-methyl-dihydro-2-furanone, oily, $[\alpha]_D$=-24.00 (CHCl$_3$), are eluted.

EXAMPLE 4

5-(3-Cyclobutyloxy-4-methoxyphenyl)-5-methyl-dihydro-2-furanone

A. 100 ml of a 0.1 M solution of samarium(II) iodide in tetrahydrofuran is mixed, with oxygen carefully excluded, with the solution of 1.30 g of 3-cyclobutyloxy-4-methoxyacetophenone, 890 mg of methyl acrylate and 625 mg of tert-butanol in 10 ml of tetrahydrofuran. The reaction solution is mixed thoroughly, allowed to stand for 16 hours at room temperature and then poured into 100 ml of 20% hydrochloric acid. It is stirred for two hours at room temperature and extracted with diethyl ether. The ether phase is washed with sodium thiosulfate solution and water, dried on sodium sulfate and concentrated by evaporation in a vacuum. The oily residue is chromatographed on a silica gel column (Kromasil 100/10 μm) with a hexane-tert-butyl methyl ether mixture (4:1). 1.0 g of (R,S)-5-(3-cyclobutyloxy-4-methoxyphenyl)-5-methyl-dihydro-2-furanone is eluted, melting point 67.6° C.

B. 600 mg of (R,S)-5-(3-cyclobutyloxy-4-methoxyphenyl)-5-methyl-dihydro-2-furanone is chromatographed on a ChiraSpher® phase (25 μm) with a hexane-dioxane mixture (15:1). 310 mg of (R)-(+)-5-(3-cyclobutyloxy-4-methoxyphenyl)-5-methyl-dihydro-2-furanone, melting point 75.7° C., $[\alpha]_D$=+30.3° (CHCl$_3$) as well as 210 mg of (S)-(-)-5-(3-cyclobutyloxy-4-methoxyphenyl)-5-methyl-dihydro-2-furanone, melting point 75.7° C., $[\alpha]_D$=-28.6° (CHCl$_3$), are eluted.

EXAMPLE 5

5-(3-Cyclopropylmethoxy-4-methoxyphenyl)-5-methyl-dihydro-2-furanone

A. 100 ml of a 0.1 M solution of samarium(II) iodide in tetrahydrofuran is mixed, with oxygen carefully excluded, with the solution of 1.06 g of 3-cyclopropylmethoxy-4-methoxyacetophenone, 890 mg of methyl acrylate and 625 mg of tert-butanol in 15 ml of tetrahydrofuran. The reaction solution is mixed thoroughly, allowed to stand for one hour at room temperature and then poured into 100 ml of 20% hydrochloric acid. It is stirred for two hours at room temperature and extracted with diethyl ether. The ether phase is washed with sodium thiosulfate solution and water, dried on sodium sulfate and concentrated by evaporation in a vacuum. The oily residue is chromatographed on a silica gel column (Kromasil 100/10 μm) with a hexane-tert-butyl methyl ether mixture (4:1). 840 mg of (R,S)-5-(3-cyclopropylmethoxy-4-methoxyphenyl)-5-methyl-dihydro-2-furanone is eluted, melting point 88.2° C.

B. 600 mg of (R,S)-5-(3-cyclopropylmethoxy-4-methoxyphenyl)-5-methyl-dihydro-2-furanone is chromatographed on a ChiraSpher® phase (25 μm) with a hexane-dioxane mixture (15:1). 310 mg of (R)-(+)-5-(3-cyclopropylmethoxy-4-methoxyphenyl)-5-methyl-dihydro-2-furanone, melting point 110.4° C., $[\alpha]_D$=+23.0° (CHCl$_3$), as well as 270 mg of (S)-(-)-5-(3-cyclopropylmethoxy-4-methoxyphenyl)-5-methyl-dihydro-2-furanone, melting point 109.4° C., $[\alpha]_D$=-24.50 (CHCl$_3$), are eluted.

EXAMPLE 6

5-(3,4-Dimethoxyphenyl)-5-methyl-dihydro-2-furanone 100 ml of a 0.1 M solution of samarium(II) iodide in tetrahydrofuran is mixed, with oxygen carefully excluded, with the solution of 710 mg of 3,4-dimethoxyacetophenone, 500 mg of methyl acrylate and 350 mg of tert-butanol in 5 ml of tetrahydrofuran. The reaction solution is mixed thoroughly, allowed to stand for two hours at room temperature and then poured into 100 ml of 20% hydrochloric acid. It is stirred for two hours at room temperature and extracted with diethyl ether. The ether phase is washed with sodium thiosulfate solution and water, dried on sodium sulfate and concentrated by evaporation in a vacuum. The oily residue is chromatographed on a silica gel column (Kromasil 100/10 μm) with a hexane-tert-butyl methyl ether mixture (4:1). 570 mg of (R,S)-5-(3,4-dimethoxyphenyl)-5-methyl-dihydro-2-furanone is eluted, melting point 71.2° C.

EXAMPLE 7

5-(3-Ethoxy-4-methoxyphenyl)-5-methyl-dihydro-2-furanone 100 ml of a 0.1 M solution of samarium(II) iodide in tetrahydrofuran is mixed, with oxygen carefully excluded, with the solution of 1.12 g of 3-ethoxy-4-methoxyacetophenone, 890 mg of methyl acrylate and 625 mg of tert-butanol in 8 ml of tetrahydrofuran. The reaction solution is mixed thoroughly, allowed to stand for 15 hours at room temperature and then poured into 100 ml of 20% hydrochloric acid. It is stirred for two hours at room temperature and extracted with diethyl ether. The ether phase is washed with sodium thiosulfate solution and water, dried on sodium sulfate and concentrated by evaporation in a vacuum. The oily residue is chromatographed on a silica gel column (Kromasil 100/10 μm) with a hexane-tert-butyl methyl ether mixture (4:1). 540 mg of (R,S)-5-(3-ethoxy-4-methoxyphenyl)-5-methyl-dihydro-2-furanone is eluted as an oily product.

EXAMPLE 8

5-(3-Cyclopentyloxy-4-methoxyphenyl)-5-ethyl-dihydro-2-furanone

A. 100 ml of a 0.1 M solution of samarium(II) iodide in tetrahydrofuran is mixed, with oxygen carefully excluded, with the solution of 1.0 g of 3-cyclopentyloxy-4-methoxypropiophenone, 500 mg of ethyl acrylate and 350 mg of tert-butanol in 10 ml of tetrahydrofuran. The reaction solution is stirred thoroughly, allowed to stand for 5 hours at room temperature and then poured into 100 ml of 20% hydrochloric acid. It is stirred for two hours at room temperature and extracted with diethyl ether. The ether phase is washed with sodium thiosulfate solution and water, dried on sodium sulfate and concentrated by evaporation in a vacuum. The residue, a yellow oil, is chromatographed on a silica gel column (Kromasil 100/10 μm) with a hexane-tert-butyl methyl ether mixture (4:1). 770 mg of oily (R,S)-5-(3-cyclopentyloxy-4-methoxy-phenyl)-5-ethyl-dihydro-2-furanone is eluted.

We claim:
1. A compound of formula I,

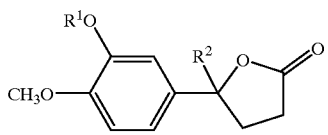

(I)

in which
R¹ means a hydrocarbon radical with up to 8 C atoms, and
R² means $C_{1-4}$ alkyl.

2. A compound of claim 1 which is (R,S)-5-(3,4-Dimethoxyphenyl)-5-methyl-dihydro-2-furanone,
(R,S)-5-(3-ethoxy-4-methoxyphenyl)-5-methyl-dihydro-2-furanone,
(R,S)-5-(4-methoxy-3-propoxyphenyl)-5-methyl-dihydro-2-furanone,
(R)-(+)-5-(4-methoxy-3-propoxyphenyl)-5-methyl-dihydro-2-furanone,
(S)-(−)-5-(4-methoxy-3-propoxyphenyl)-5-methyl-dihydro-2-furanone,
(R,S)-5-(3-isobutyloxy-4-methoxyphenyl)-5-methyl-dihydro-2-furanone,
(R)-(+)-5-(3-isobutyloxy-4-methoxyphenyl)-5-methyl-dihydro-2-furanone,
(S)-(−)-5-(3-isobutyloxy-4-methoxyphenyl)-5-methyl-dihydro-2-furanone,
(R,S)-5-(3-cyclopropylmethyloxy-4-methoxyphenyl)-5-methyl-dihydro-2-furanone,
(R)-(+)-5-(3-cyclopropylmethyloxy-4-methoxyphenyl)-5-methyl-dihydro-2-furanone,
(S)-(−)-5-(3-cyclopropylmethyloxy-4-methoxyphenyl)-5-methyl-dihydro-2-furanone,
(R,S)-5-(3-cyclobutyloxy-4-methoxyphenyl)-5-methyl-dihydro-2-furanone,
(R)-(+)-5-(3-cyclobutyloxy-4-methoxyphenyl)-5-methyl-dihydro-2-furanone,
(S)-(−)-5-(3-cyclobutyloxy-4-methoxyphenyl)-5-methyl-dihydro-2-furanone,
(R,S)-5-(3-cyclopentyloxy-4-methoxyphenyl)-5-methyl-dihydro-2-furanone,
(R)-(+)-5-(3-cyclopentyloxy-4-methoxyphenyl)-5-methyl-dihydro-2-furanone,
(S)-(−)-5-(3-cyclopentyloxy-4-methoxyphenyl)-5-methyl-dihydro-2-faranone, or
(R,S)-5-(3-cyclopentyloxy-4-methoxyphenyl)-5-ethyl-dihydro-2-furanone.

3. A pharmaceutical agent which comprises a compound according to claim 1 and a pharmaceutically acceptable carrier.

4. A method of treating a disease mediated by activation of the tumor necrosis factor, comprising administering an effective amount of a compound according to claim 1 to a patient in need of such treatment.

5. A method of treating multiple sclerosis, comprising administering an effective amount of a compound according to claim 1 to a patient in need of such treatment.

6. A process for the production of a compound according to claim 1, comprising
a) reacting a compound of formula II,

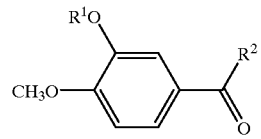

(II)

in which R1 and R2 have the meaning as in claim 1, with an acrylic acid ester in the presence of samarium (II) iodide and a proton donor, and
b) optionally seperating the isomers.

7. The compound of claim 1, wherein said hydrocarbon radical R¹ is alkyl, alkenyl, alkinyl, cycloalkyl or cycloalkylalkyl.

8. The compound of claim 7, wherein said alkyl has up to 6 C atoms and is straight-chain or branched.

9. The compound of claim 7, wherein said alkenyl or alkinyl has up to 4 C atoms.

10. The compound of claim 9, wherein said alkenyl or alkinyl is vinyl, 1-propenyl, 2-propenyl, 3-methyl-2-propenyl or 2-propinyl.

11. The compound of claim 7, wherein said cycloalkyl is cyclopropyl, cyclobutyl, cyclopentyl, cyclohexyl or cycloheptyl.

12. The compound of claim 7, wherein said cycloalkyl alkyl is $C_{3-7}$ cycloalkyl-$C_{1-2}$ alkyl, cyclopropylmethyl, cyclopropylethyl or cyclopentylmethyl.

13. The compound of claim 1, wherein said hydrocarbon radical R² is straight-chain or branched.

14. The compound of claim 1, which is in the form of a mixture of enantiomers.

15. The compound of claim 14, which is in the form of a racemic mixture.

16. The compound of claim 1, which is the form of a single enantiomer.

17. The compound of claim 16, which is a (+) enantiomer.

18. The compound of claim 16, which is a (−) enantiomer.

19. A method of treating rheumatoid arthritis, arthritis, and osteoarthritis, comprising administering an effective amount of a compound according to claim 1 to a patient in need of such treatment.

* * * * *